United States Patent [19]
Ohnishi

[11] Patent Number: 5,959,133
[45] Date of Patent: Sep. 28, 1999

[54] PROCESS FOR THE PREPARATION OF PLATINUM COMPOUNDS

[75] Inventor: Yuko Ohnishi, Kanagawa-ken, Japan

[73] Assignee: Tanaka Kikinzoku Kogyo K.K., Tokyo, Japan

[21] Appl. No.: 09/029,682

[22] PCT Filed: Jul. 4, 1997

[86] PCT No.: PCT/JP97/02332

§ 371 Date: Mar. 3, 1998

§ 102(e) Date: Mar. 3, 1998

[87] PCT Pub. No.: WO98/01454

PCT Pub. Date: Jan. 15, 1998

[30] Foreign Application Priority Data

Jul. 4, 1996 [JP] Japan .................................. 8-174788

[51] Int. Cl.$^6$ ............................................. C07F 15/00
[52] U.S. Cl. .................................................. 556/137
[58] Field of Search ................................... 556/137

[56] References Cited

U.S. PATENT DOCUMENTS

| | | |
|---|---|---|
| 4,115,418 | 9/1978 | Gale . |
| 4,140,707 | 2/1979 | Cleare . |
| 4,169,846 | 10/1979 | Kidani . |
| 4,452,812 | 6/1984 | Macquet ................. 556/137 |
| 4,665,210 | 5/1987 | Bitha ....................... 556/137 |
| 4,710,557 | 12/1987 | Kidani ..................... 556/137 |
| 5,011,959 | 4/1991 | Khokhar .................. 556/137 |
| 5,298,642 | 3/1994 | Tozawa .................... 556/137 |
| 5,338,874 | 8/1994 | Nakanishi ................ 556/137 |
| 5,420,319 | 5/1995 | Okamoto .................. 556/137 |

OTHER PUBLICATIONS

CA:120:144135 abs of JP05194332, Aug. 3, 1993.
J Med Chem vol. 21 No. 12 "Antitumor Activity of 1,2 Diaminocyclohexane–Platinum complexes against Sarcoma 180 Ascites Form" by Kidani pp. 1315–1318, 1978.
Inorg Chem vol. 27 No. 23 Synthesis and characterization of Diasteromeric (1,2–diaminocyclohexane) platinum (II) complexes, by Hoeschele pp. 4106–4113, 1988.

*Primary Examiner*—Gary Geist
*Assistant Examiner*—Jean F. Vollano
*Attorney, Agent, or Firm*—Jordan and Hamburg LLP

[57] ABSTRACT

A process for the preparation of cis-platinum(II) complexes of 1,2-cyclohexanediamine isomers, represented by formula I, containing substantially no dihydroxoplatinum(IV) complex as an impurity.

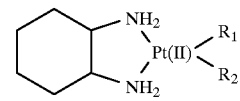

(I)

Deoxygenated water is used in all steps of the process, from charging of the starting materials; i.e., potassium tetrachloroplatinate and trans-(-)-1,2-cyclohexanediamine, to the acquisition of target complexes. In addition, a low-oxygen content atmosphere is applied as an operational environment to prevent deoxygenated water from degradation through oxygen absorption and to eliminate the possibility of direct oxidation of a platinum compound due to atmospheric oxygen.

3 Claims, No Drawings

PROCESS FOR THE PREPARATION OF PLATINUM COMPOUNDS

This application is the national stage of PCT/JP97/02332 filed Jul. 4, 1997.

BACKGROUND OF THE INVENTION

1. Field of the Invention

The present invention relates to a process for the preparation of cis-platinum(II) complexes of 1,2-cyclohexanediamine isomers that serve as active components of carcinostatic drugs.

2. Background Art

Platinum compounds represented by formula I

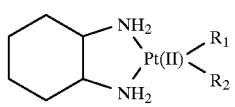

(I)

are generally known to have carcinostaticity. They have conventionally been prepared by the following steps: reacting $K_2Pt(II)X_4$ (X is Cl or Br) with a 1,2-cyclohexanediamine isomer to form an intermediate compound represented by formula II

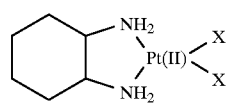

(II)

dissolving the intermediate compound in water under boiling; adding thereto a solution of $AgNO_3$ in an amount of twice the mol equivalent of the intermediate compound represented by formula II so as to cause chlorine or bromine contained in the compound to precipitate in the form of silver chloride or bromide; separating the precipitates through filtration; and adding a dibasic organic acid to the filtrate.

However, the platinum compounds represented by formula I obtained through the customary process contain as an impurity about 0.1–5% of a dihydroxoplatinum(IV) complex—a platinum compound represented by formula III—which is produced through oxidation of the platinum compounds represented by formula I.

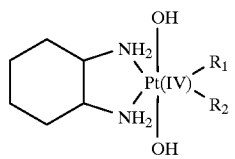

(III)

SUMMARY OF THE INVENTION

In view of the foregoing, a general object of the present invention is to provide a process for a preparation of cis-platinum(II) complexes of 1,2-cyclohexanediamine isomers that contain substantially no dihydroxoplatinum(IV) complex as an impurity.

To achieve the above object, the inventor of the present invention has conducted careful studies of a process for a preparation of cis-platinum (II) complexes of 1,2-cyclohexanediamine isomers to overcome the aforementioned problems and has developed a process which does not produce the aforementioned impurity, i.e., dihydroxoplatinum(IV) complex, by satisfactorily eliminating factors that cause oxidation during the preparation.

According to the present invention, the target compounds which serve as active components of carcinostatic drugs, i.e., cis-platinum(II) complexes of 1,2-cyclohexanediamine isomers, are prepared from potassium tetrachloroplatinate and trans-(-)-1,2-cyclohexanediamine, and oxidation of the target complexes is prevented by the process described below.

The preparation steps of the present invention have two characteristics. Firstly, deoxygenated water is used to prevent oxidation caused by dissolved oxygen in the solution where cis-platinum(II) complexes of 1,2-cyclohexanediamine isomers are being formed. Secondly, the oxygen content in the operational atmosphere involved in the preparation of the platinum compounds is reduced in order to eliminate possibility of direct oxidation of cis-platinum(II) complexes of 1,2-cyclohexanediamine isomers due to atmospheric oxygen as well as to prevent degradation of deoxygenated water. Deoxygenated water degrades as it absorb oxygen.

The process of the present invention provides cis-platinum(II) complexes of 1,2-cyclohexanediamine isomers which contain substantially no physiologically active dihydroxoplatinum(IV) complex as an impurity.

DETAILED DESCRIPTION OF PREFERRED EMBODIMENTS

According to the process of the present invention for preparing platinum(II) complexes of 1,2-cyclohexanediamine isomers represented by formula I, there is employed deoxygenated water in all steps of preparing a platinum compound from the starting materials, i.e, potassium tetrachloroplatinate and trans-(-)-1,2-cyclohexanediarnine, and substituting nitrogen or an inert gas for air of the operational environment or alternatively degassing under vacuum to thereby produce a low-oxygen content atmosphere so as to prevent degradation of deoxygenated water and to eliminate a possibility of direct oxidation of a platinum compound due to oxygen contained in air of the operational environment.

In the process, deoxygenated water is consistently used in all steps from the placement of the starting materials, i.e., potassium tetrachloroplatinate and trans-(-)-1,2-cyclohexanediamine, to the target cis-platinum(II) complexes of 1,2-cyclohexanediamine isomers. Therefore, oxidation due to oxygen dissolved in the deoxygenated water is prevented, and dihydroxoplatinum(IV) complex, an impurity, is not formed.

It has empirically been determined that the oxygen content in an operational environment should be adjusted to 5% or less in order to prevent deoxygenated water from absorbing oxygen and being degraded by atmospheric oxygen. To attain this oxygen content, air of the operational environment is preferably evacuated through degassing under vacuum or replacement with nitrogen or an inert gas.

The best mode of the embodiments of the present invention will now be described. In the process of the present invention for the preparation of platinum(II) complexes of 1,2-cyclohexanediamine isomers, deoxygenated water was used consistently as water participating in the reactions, and the atmosphere of operational chamber having the oxygen content level of 1% adjusted through nitrogen-substitution was provided during all steps of preparing cis-platinum(II) complexes of 1,2-cyclohexanediamine isomers—active components of carcinostatic drugs—from the starting materials, i.e., potassium tetrachloroplatinate and trans-(-)-1,2-cyclohexanediamine.

Potassium tetrachloroplatinate (562.5 g) and trans-(-)-1,2-cyclohexanediamine (154.8 g) were dissolved and mixed in deoxygenated water (3.5 l) to thereby obtain cis-dichloro (trans-(-)-1,2-cyclohexanediamine)platinum(II) without recrystallization (cake-like, yield 96%). The resultant material was suspended in deoxygenated water (5.7 l) and the resulting suspension was mixed with a solution of silver nitrate (386.4 g) dissolved in deoxygenated water (2.8 l). This solution was stirred in the dark at room temperature for three days, then silver chloride that precipitated was mostly removed through filtration. The filtrate was concentrated under reduced pressure, and subsequently, a solution of potassium iodide (3.85 g) dissolved in deoxygenated water (45 ml) was added thereto. The resultant solution was stirred for one hour, after which activated carbon was added thereto. Formed precipitates and activated carbon were completely removed through filtration. Oxalic acid (146.3 g) was added to the filtrate, then the solution was allowed to stand for 2 hours to thereby obtain cis-oxalato(trans-(-)-1,2-cyclohexanediamine)platinum(II) (crude crystals, yield 50%). The crude crystals (270 g) were dissolved in deoxygenated water (12 l) with heat, then the solution was filtered and cooled to room temperature. White crystals that precipitated were collected by filtration, washed with a small amount of deoxygenated water, and dried to thereby obtain the target complex, cis-oxalato(trans-(-)-1,2-cyclohexanediamine)platinum(II) (160 g).

In a comparative example, the same procedure as described above was performed except that oxygen-containing water was used during all steps until the target cis-platinum(II) complexes of 1,2-cyclohexanediamine isomers are obtained from potassium tetrachloroplatinate and trans-(-)-1,2-cyclohexanediamine as starting materials, and that the reactions were carried out in the atmosphere.

A purity analysis was carried out for cis-oxalato(trans-(-)-1,2-cyclohexanediamine)platinum(II) obtained from the working example of the present invention and for the corresponding complex obtained from the comparative example, through high-performance liquid chromatography (HPLC) (ODS column length, 50 cm; mobile phase, water-acetonitrile mixture; flow of eluent, 5 ml/min).

From the results of the HPLC purity analysis, a dihydroxoplatinum(IV) complex was detected in an amount of 1.5% in the cis-oxalato(trans-(-)-1,2-cyclohexanediamine)platinum(II) prepared in the comparative example, whereas no dihydroxoplatinum(IV) complex was detected in the corresponding compound prepared in the working example of the present invention.

What is claimed is:

1. A process for a preparation of a platinum(II) complex of a 1,2-cyclohexanediamine isomer represented by formula I

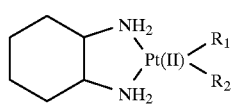

(I)

wherein the steric configuration of 1,2-cyclohexanediamine is cis, trans-d, or trans-l and $R_1$ and $R_2$ form a cyclic structure with Pt(II) to represent a group of formula IV, formula V, formula VI, formula VII, formula VIII, or formula IX; the process comprising use of deoxygenating water in all steps for obtaining a platinum compound from potassium tetrachloroplatinate and trans-(-)-1,2-cyclohexanediamine serving as starting materials, and substituting nitrogen for air of an operational environment to thereby produce a low-oxygen content atmosphere so as to prevent degradation of deoxygenated water and to eliminate a possibility of direct oxidation of a platinum compound due to oxygen contained in air of the operational environment

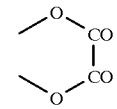

(IV)

(V)

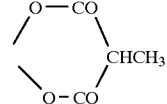

(VI)

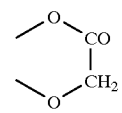

(VII)

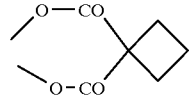

(VIII)

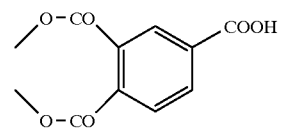

(IX)

2. A process for a preparation of a platinum(II) complex of a 1,2-cyclohexanediamine isomer represented by formula I

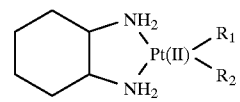

(I)

wherein the steric configuration of 1,2-cyclohexanediamine is cis, trans-d, or trans-l, and $R_1$ and $R_2$ form a cyclic structure with PT(II) to represent a group of formula IV, formula V, formula VI, formula VII, formula VIII, or formula IX; the process comprising use of deoxygenating water in all steps for obtaining a platinum compound from potassium tetrachloroplatinate and trans-(-)-1,2-cyclohexanediamine serving as starting materials, and substituting an inert gas for air of an operational environment to thereby produce a low-oxygen content atmosphere so as to prevent degradation of deoxygenated water and to eliminate a possibility of direct oxidation of a platinum compound due to oxygen contained in air of the operational environment

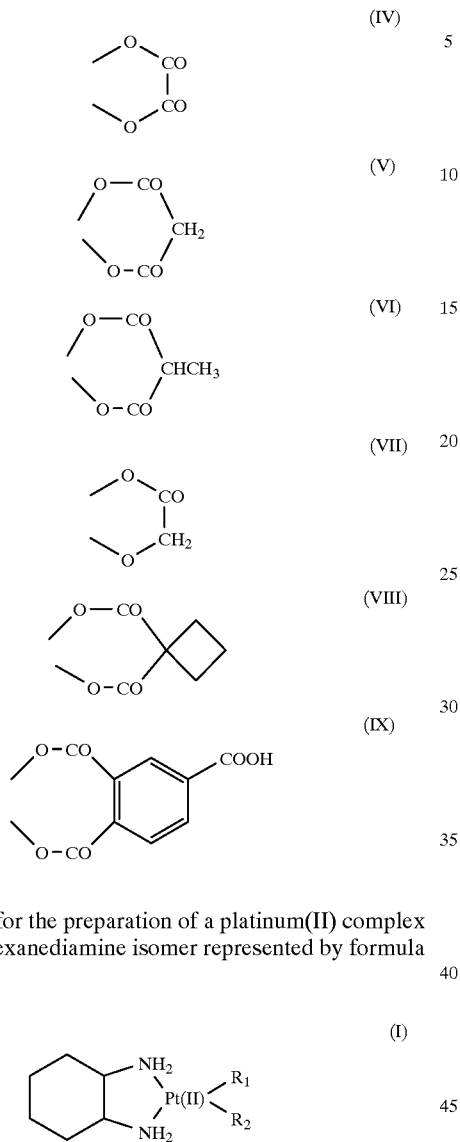

3. A process for the preparation of a platinum(II) complex of a 1,2-cyclohexanediamine isomer represented by formula I wherein the steric configuration of 1,2-cyclohexanediamine is cis, trans-d, or trans-l, and $R_1$ and $R_2$ form a cyclic structure with Pt(II) to represent a group of formula IV,
formula V, formula VI, formula VII, formula VIII, or formula IX; the process comprising use of deoxygenating water in all steps for obtaining a platinum compound from potassium tetrachloroplatinate and trans-(-)-1,2-cyclohexanediamine serving as starting materials, and degassing under vacuum air of an operational environment to thereby produce a low-oxygen content atmosphere so as to prevent degradation of deoxygenated water and to eliminate a possibility of direct oxidation of a platinum compound due to oxygen contained in air of the operational environment

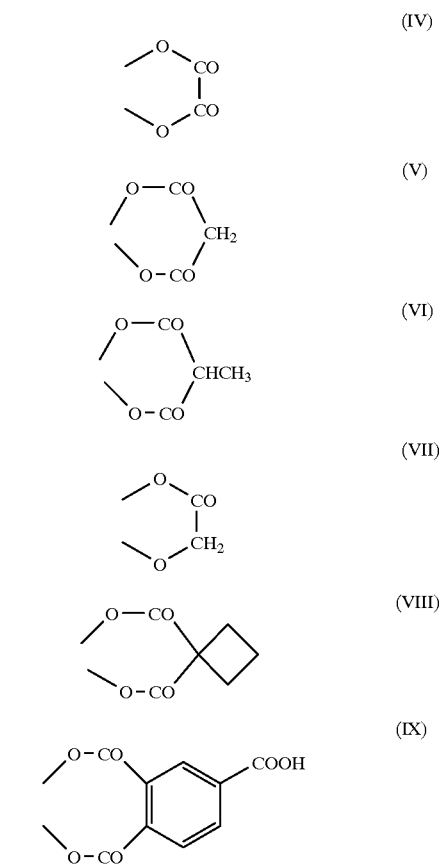

* * * * *